United States Patent [19]
Fischer et al.

[11] Patent Number: 5,168,156
[45] Date of Patent: Dec. 1, 1992

[54] REFLECTIVE EVANESCENT FIBER-OPTIC CHEMICAL SENSOR

[75] Inventors: George Fischer, Shaker Hts., Ohio; Lloyd W. Burgess, Jr., Seattle, Wash.

[73] Assignee: The Standard Oil Company, Cleveland, Ohio

[21] Appl. No.: 722,955

[22] Filed: Jun. 28, 1991

[51] Int. Cl.⁵ .................. H01J 5/16; G01N 21/00
[52] U.S. Cl. .................. 250/227.21; 250/227.14; 250/227.24; 356/436; 356/133; 385/12
[58] Field of Search .................. 250/227.14, 227.21, 250/227.24, 231.10, 900–907; 356/73, 73.1, 44, 133, 445, 448, 433, 436, 432; 385/12, 43

[56] References Cited

U.S. PATENT DOCUMENTS

| | | | |
|---|---|---|---|
| Re.33,789 | 1/1992 | Stevenson | 356/133 |
| 4,312,562 | 1/1982 | Segawa et al. | 350/96.15 |
| 4,433,291 | 2/1984 | Yarviv et al. | 350/96.29 |
| 4,514,054 | 4/1985 | Stowe | 356/345 |
| 4,560,248 | 12/1985 | Cramp et al. | 356/402 |
| 4,582,809 | 4/1986 | Block et al. | 356/73.1 |
| 4,596,925 | 6/1986 | Gilby | 250/227.21 |
| 4,599,711 | 7/1986 | Cuomo | 250/227.21 |
| 4,668,861 | 5/1987 | White | 250/227 |
| 4,755,054 | 7/1988 | Ferree | 356/418 |
| 4,778,237 | 10/1988 | Sorin | 350/96.15 |
| 4,783,137 | 11/1988 | Kosman et al. | 350/96.16 |
| 4,786,130 | 11/1988 | Georgiou et al. | 350/96.15 |
| 4,827,121 | 5/1989 | Vidrine, Jr. et al. | 356/346 |
| 4,830,451 | 5/1989 | Stone | 356/352 |
| 4,834,496 | 5/1989 | Blyler, Jr. | 250/227 |
| 4,834,497 | 5/1989 | Angel | 350/96.15 |
| 4,851,665 | 7/1989 | Pesavento et al. | 250/227.23 |
| 4,895,421 | 1/1990 | Kim et al. | 350/96.15 |
| 4,904,940 | 2/1990 | Rempt | 356/345 |
| 4,907,857 | 3/1990 | Giuliani et al. | 250/231.10 |
| 4,972,076 | 11/1990 | Willson | 250/227.21 |
| 5,015,843 | 5/1991 | Seitz et al. | 250/227.21 |

FOREIGN PATENT DOCUMENTS 0061884 10/1982 European Pat. Off. .

OTHER PUBLICATIONS

"Underground Storage Tanks", Photonics Spectra 81, Apr. 1991.

*Primary Examiner*—Davis L. Willis
*Assistant Examiner*—Hoa Q. Pham
*Attorney, Agent, or Firm*—Larry W. Evans; John E. Miller; Teresan W. Gilbert

[57] ABSTRACT

A fiber-optic sensor is formed from three optical fibers. The distal ends of the fibers are optically linked by bonding their cores and directing their ends to mirrors. A portion of one of the fibers near the bonded point is exposed directly to the fluid to be sensed. The transmission characteristics of this fiber, the signal fiber, is then affected by the chemical constituents of the fluid. Light directed into the proximal end of one of the other fibers, the input fiber, is split between the signal fiber and the remaining fiber, the reference fiber. The ratio of the light in the signal fiber to the light in the reference fiber provides an indication of the chemical constituents that minimizes errors introduced by factors such as bends in the fibers and temperature.

19 Claims, 3 Drawing Sheets

5,168,156

REFLECTIVE EVANESCENT FIBER-OPTIC CHEMICAL SENSOR

BACKGROUND OF THE INVENTION

This invention relates to chemical detection and, in particular, to chemical detection done by optical techniques.

Chemical detection is a necessity for many applications, particularly, as new chemical processes are developed and environmental concerns increase. Simple, rugged, inexpensive sensors are needed for industrial process control and environmental monitoring.

European Patent EP 0 061 884 A1 discloses a device for detecting changes in chemical or physical parameters using an optical fiber sensor and is incorporated herein in its entirety by reference. In the described device, the core of the fiber is surrounded by a cladding whose absorption spectrum varies with the composition of the surrounding material to be sensed. Light or photons enter one end of the fiber. The light exiting the other end of the fiber varies according to the chemical characteristics of the material in contact with the cladding. This results from coupling into the evanescent field of fiber.

Such a device provides both a rugged and compact sensor. However, in many real-world applications it can be difficult and/or time consuming to calibrate the sensor for a particular test environment. For example, tight bends in the sensor fiber can substantially alter the transmission characteristics of the fiber. Similarly, the temperature of the fiber affects the transmission. In some cases, it may even be difficult to determine if the fiber has been broken. In addition, noise and drift in the light source may cause erroneous readings.

SUMMARY OF THE INVENTION

The present invention provides a fiber-optic sensor that allows easy detection of a severed sensor and automatic compensation for variations in sensor output due to extraneous factors such as variations in source intensity, fiber routing and temperature.

The fiber-optic sensor includes an input fiber having a proximal and distal portion; a reference output fiber having a proximal and distal portion and a signal output fiber having a proximal portion, a distal portion and a sensing portion therebetween. The distal portions of the fibers are in optical communication, wherein a part of a plurality of photons introduced into the input fiber proximal portion travels to the proximal portions of the reference output fiber and the signal output fiber.

In the preferred embodiment, the sensor further includes at least one reflector proximate the distal portions for reflecting photons from the fibers towards the proximal portions. The core of the distal portion of the signal output fiber and the core of the distal portion of the reference output fiber are fused with the core of the distal portion of the input fiber.

Further, the distal portion of each fiber may be reflectively coated and the fused cores covered with a cladding material.

The sensor can be formed from an elongated hermetic housing having a proximal and distal end and a wall; an input fiber entering the proximal end of the housing and having a proximal and distal portion; a reference output fiber entering the proximal end of the housing and having a proximal and distal portion; a signal output fiber entering the proximal end of the housing and having a proximal portion, a distal portion and a sensing portion therebetween. The signal output fiber exits the member through the wall and reenters the member through the wall. The sensing portion thereby being located external to the member. The distal portions of the fibers are in optical communication, whereby a part of a plurality of photons introduced into the input fiber proximal portion travels to the proximal portions of the reference output fiber and the signal output fiber.

The member may be a hollow metal cylinder having a hole at the proximal end and two holes in the wall. The fibers enter through the hole at the proximal end and the signal output fiber exits through one of the holes in the wall and reenters through the other. Each of the holes is sealed with a sealant.

The sensing portion of the sensor changes transmission characteristics in response to chemical constituents of a fluid to be sensed. This portion may be the signal output fiber with the fiber jacket or both the jacket and the fiber cladding removed. In addition, a membrane may be added to the sensing portion where the membrane selectively allows constituents of the fluid to be sensed to contact the signal output fiber.

The fiber-optic sensor system includes the sensor as well as a light source for transmitting light into the proximal portion of the input fiber, a reference sensor for sensing light from the proximal portion of the reference output fiber and providing a reference signal in response thereto, a signal sensor for sensing light from the proximal portion of the signal output fiber and providing a sensor signal in response thereto, a dividing means for forming the ratio of the sensor signal to the reference signal. This ratio indicates the concentration of the material to be sensed.

DESCRIPTION OF THE PREFERRED EMBODIMENTS

Figure 1:
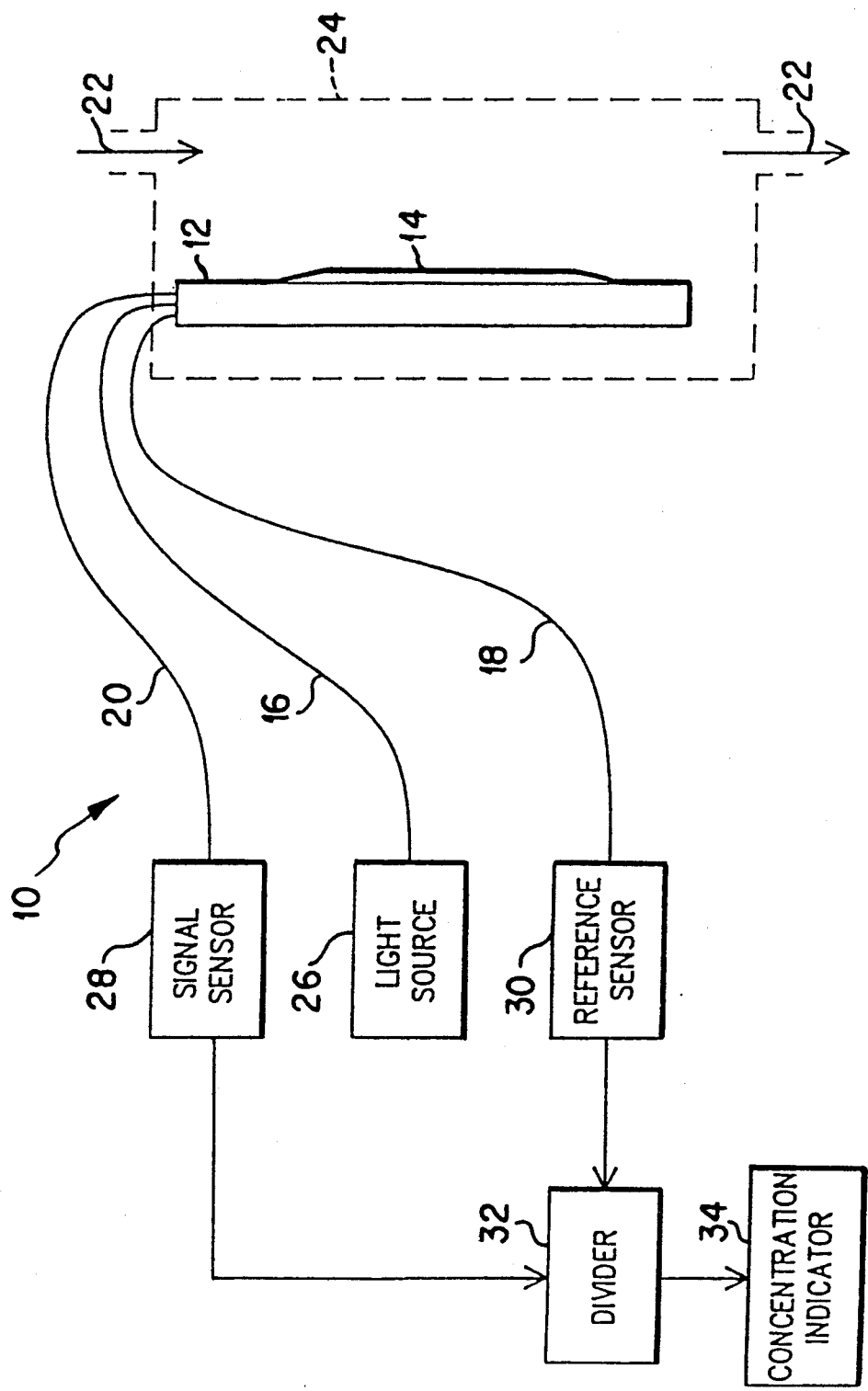
FIG. 1 is a block diagram of a fiber-optic sensor system according to the invention.

Referring to FIG. 1, a fiber-optic sensor system 10 is shown. A fiber-optic sensor 12 has a chemical sensing portion 14. An input fiber 16, a reference fiber 18 and a signal fiber 20 enter the sensor 12. The fibers 16, 18, 20 may be, for example, Fiberguide Industries Model SPC200N, a nylon jacketed fiber with a silicon dioxide core and plastic cladding.

A fluid 22 (e.g., a gas, liquid or vapor) that contains a chemical to be sensed comes in contact with the sensing portion 14. A chamber 24 may be provided about the sensor 12 to contain the fluid 22 about the sensor 12 and/or exclude other fluids.

A light source 26 is connected to the input fiber 16. The input of a signal sensor 28 is connected to the signal fiber 20. The input of a reference sensor 30 is connected to the reference fiber 18. The light source may be, for example, one or more light-emitting diodes. The sensors 28, 30 may be, for example, photodiodes.

The output of the signal sensor 28 is connected to the dividend input of a divider 32. The output of the reference sensor 30 is connected to the divisor input of the divider 32. The divider 32 may be, for example, an analog divider circuit, a combination of digital-to-analog converters and a digital computer, or other means to perform the desired division. In the preferred embodiment, the use of a digital computer to perform the division also permits automatic self-diagnosis and calibration under control of the computer.

The quotient or ratio output of the divider 32 is connected to a concentration indicator 34, which may be, for example, a signal light, alarm circuit, meter, digital display or a circuit for initiating some action in response to the ratio output.

Figure 2:
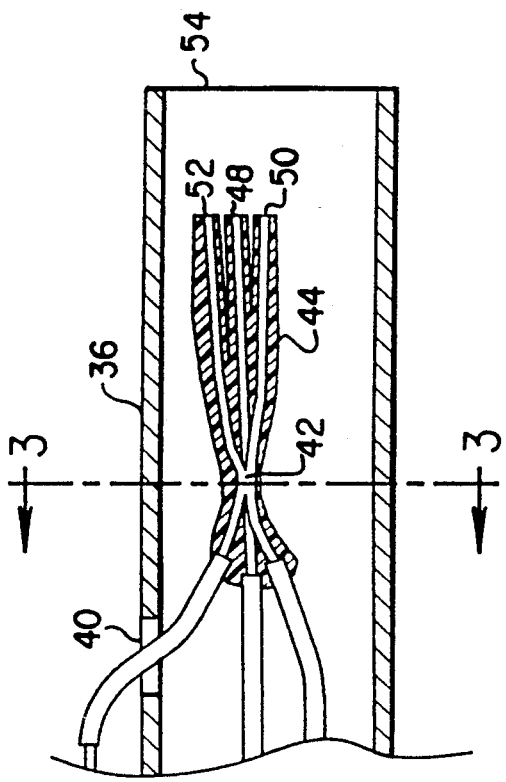
FIG. 2 is a side elevation view of a sensor according to the invention with portions cut away.

Referring to FIG. 2, the sensor 12 is shown with portions cut-away. The fibers 16, 18, 20 enter the end 35 of a hollow metallic tube 36. The signal fiber 20 exits the tube 36 through a hole 38 in the wall of the tube 36. The signal fiber 20 reenters the tube 36 through a hole 40 in the wall of the tube 36. The tube 36 may be, for example, 15 cm in length, 1.5 mm in diameter and made of brass. The holes 38, 40 may be, for example, spaced 8 cm apart.

The sensing portion 14 of the signal fiber 20 may be formed by removing the jacket from the signal fiber 20. Alternatively, the cladding may also be removed depending on which alternative gives that best results for the chemical material to be sensed. Further selectivity can be achieved by either coating the stripped fiber with a membrane that selectively passes the chemical of interest or by simply separating the fluid 22 from the sensor with a membrane.

The fibers 16, 18, 20 are optically linked or communicating at a common point 42 near their distal ends. This may be accomplished by removing the jacket and cladding from the distal end portion of the fibers 16, 18, 20 and fusing the exposed cores together at the point 42.

If desired, the end portions may be re-clad, for example, by dipping them into a silicone rubber cladding material. This results in some loss of coupling between the fibers, but provides more positive isolation from the fluid 22.

Figure 3:
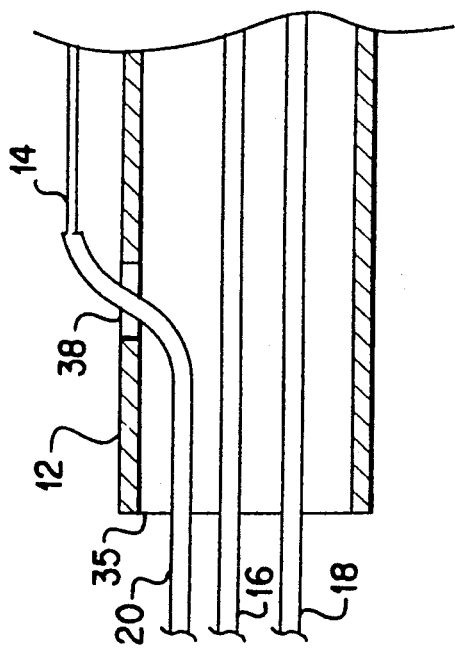
FIG. 3 is a cross sectional view along the line 3-3 in FIG. 2.

Referring to FIG. 3, a cross section of the sensor 12 at the point 42 is shown. The cores of the fibers 16, 18, 20 have been fused into a single core 46.

This linking between the fibers 16, 18, 20 effectively creates two light paths: a reference light path via the input fiber 16 and the reference fiber 18; and a signal light path via the input fiber 16 and the signal fiber 20.

Figure 4:
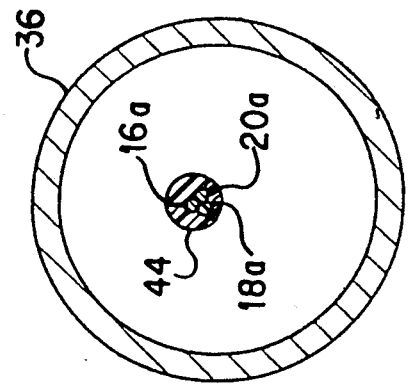
FIG. 4 is a cross sectional view similar to FIG. 3 of an additional embodiment of the invention.

As a less effective alternative, the cores of the fibers 16, 18, 20 may be cemented together at the common point 42. For example, Norland optical cement may be used. FIG. 4 shows the cores 16a, 18a, 20a of the fibers 16, 18, 20, respectively, cemented together. Once again, the end portions may be re-clad by dipping them into a silicone rubber cladding material.

The distal ends of the fibers 16, 18, 20 are covered by mirrors 48, 50, 52, respectively. The mirrors 48, 50, 52 may be, for example, aluminum vapor deposited onto the end surfaces of the fibers 16, 18, 20.

While inefficient, it is also possible to have the fibers 16, 18, 20 communicate by directing the end of each fiber towards a single reflector/diffuser spaced from the ends.

The ends 35, 54 of the tube 36 and the holes 38, 40 in the wall of the tube 36 may be advantageously sealed with, for example, epoxy sealant (unshown). This hermetically seals the interior of the tube 36 from the fluid 22. In addition, the fibers 16, 18, 20 may be advantageously bundled together to ensure that they are subjected to substantially the same physical conditions.

In operation, the light source 26 transmits light or photons towards the distal end of the input fiber 16. The combination of the mirrors 48, 50, 52 and the common point 42 results in part of this light entering the reference fiber 18 and the signal fiber 20.

The light in the reference fiber 18 travels to the reference sensor 30 where it is converted to an electrical signal and passed to the divisor input of the divider 32.

The light in the signal fiber 20 travels to the signal sensor 28 except that this light is attenuated depending on the chemical constituents of the fluid 22 that are in contact with the sensor portion 14 of the signal fiber 20. The signal sensor 28 converts the received light to an electrical signal and provides this signal as an input to the dividend input of the divider 32.

The divider 32 forms the ratio of the signal fiber light to the reference fiber light and provides the ratio or quotient to the concentration indicator 34. In the preferred embodiment, the divider 32 includes a digital computer that performs automatic self-diagnosis on the sensor 30. The indicator 34 can be used to control a process on a continuous basis or to provide an alarm.

The reference and signal light paths are both subject to the same temperatures and mechanical conditions (e.g., bending), but the reference light path does not include a sensing portion. As a result, the variation of the reference light path can be used to calibrate the variation of the signal light path so that only the response to the sensor portion 14 to the fluid 22 is observed.

Forming the ratio of the signal fiber light to the reference fiber light is the simplest way to do this, though more sophisticated ways are possible. The ratio method provides both good common mode interference and noise rejection.

In addition, if the connections to the sensor 12 are severed, it is readily apparent as no light is returned on the reference fiber 18. This condition is thus easily distinguishable from the sensor portion 14 being "saturated."

It should be noted that another advantage of the sensor 12 is that because no fiber loop is required, the sensor can be very narrow (little more than the combined diameters of the fibers).

Figure 5:
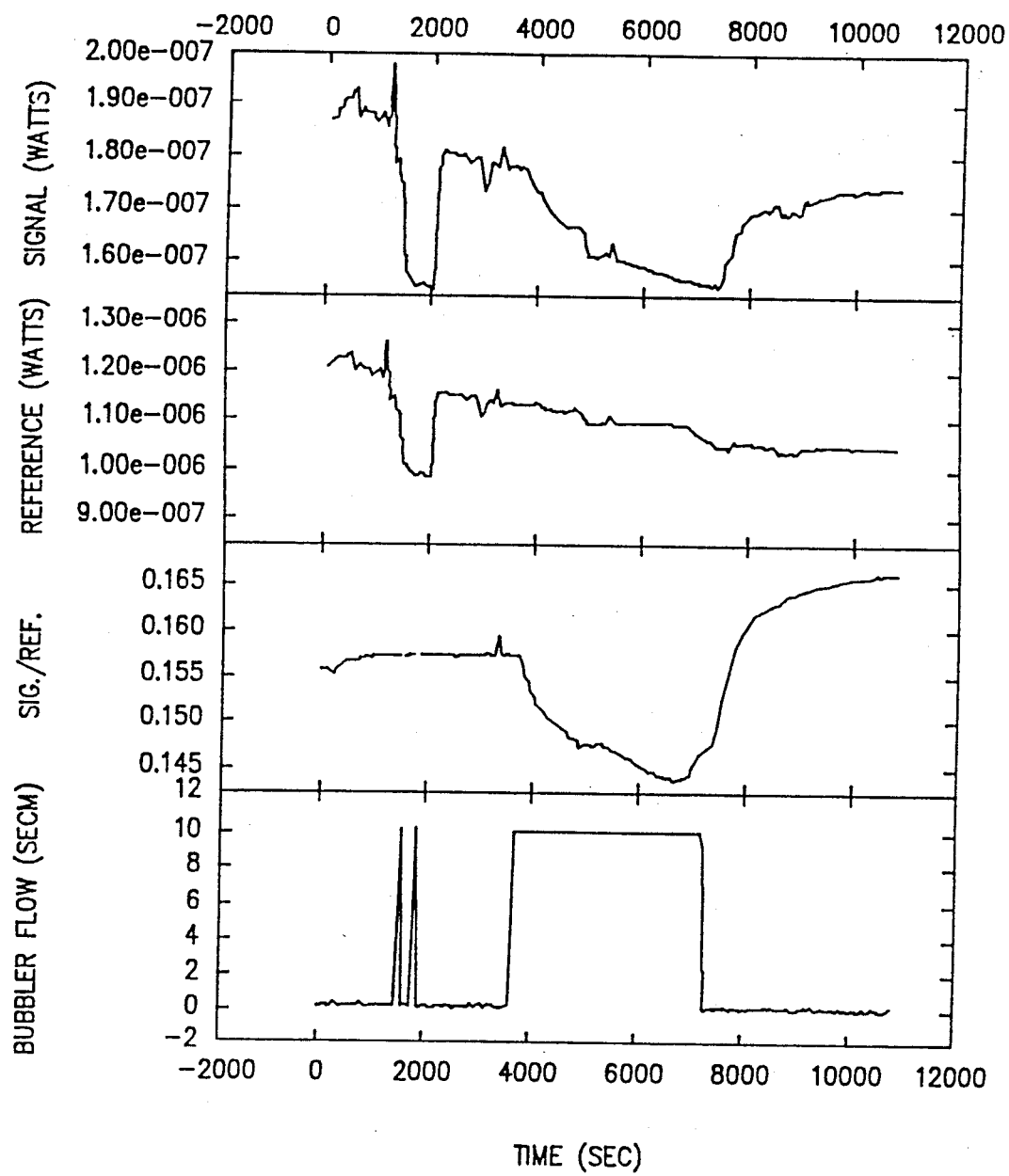
FIG. 5 is an exemplary graph of the performance of the invention.

Referring to FIG. 5, an exemplary graph of the fiber-optic sensor system 10 in operation is shown. At about 3,700 seconds, a bubbler supplied toluene vapor to the sensor 12. This results in a decrease in the light through the signal light path, but not a dramatic one compared to the noise levels.

However, when the ratio of the signal fiber light to the reference fiber light is formed (SIG./REF.), a dramatic response occurs.

It is particularly interesting to note that at about 1,700 seconds, two noise spikes unrelated to the test were encountered. These spikes are manifested in the bubbler flow graph, the signal graph and the reference graph but are largely eliminated in the ratio (SIG./REF.) graph.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A fiber-optic sensor comprising:
   an input fiber having a proximal and distal portion;
   a reference output fiber having a proximal and distal portion; and
   a signal output fiber having a proximal portion, a distal portion and a sensing portion therebetween, the distal portions of said fibers being in optical communication and said sensing portion being adjacent to said distal portions, wherein a part of a plurality of photons introduced into said input fiber proximal portion travels to the proximal portions of said reference output fiber and signal output fiber.

2. A fiber-optic sensor according to claim 1, further comprising at least one reflector proximate said distal portions for reflecting photons from said fibers towards said proximal portions and wherein each fiber has a core, the core of the distal portion of the signal output fiber and the core of the distal portion of the reference output fiber being optically linked by an adhesive to the core of the distal portion of the input fiber.

3. A fiber-optic sensor according to claim 2, wherein the distal portion of each fiber has an end, said end being reflectively coated.

4. A fiber-optic sensor according to claim 1, further comprising at least one reflector proximate said distal portions for reflecting photons from said fibers towards said proximal portions and wherein each fiber has a core, the core of the distal portion of the signal output fiber and the core of the distal portion of the reference output fiber being fused with the core of the distal portion of the input fiber.

5. A fiber-optic sensor according to claim 4, wherein the distal portion of each fiber has an end, said end being reflectively coated.

6. A fiber-optic sensor according to claim 4, wherein the fused cores are covered with a cladding material.

7. A fiber-optic sensor comprising:
   an elongated hermetic housing having a proximal and distal end and a wall,
   an input fiber entering the proximal end of the housing and having a proximal and distal portion;
   a reference output fiber entering the proximal end of the housing and having a proximal and distal portion; and
   a signal output fiber entering the proximal end of the housing and having a proximal portion, a distal portion and a sensing portion therebetween, said signal output fiber exiting said housing through said wall and reentering said housing through said wall, said sensing portion thereby being located external and adjacent to said housing, the distal portions of said fibers being in optical communication, whereby a part of a plurality of photons introduced into said input fiber proximal portion travels to the proximal portions of said reference output fiber and signal output fiber.

8. A fiber-optic sensor according to claim 7, wherein said housing comprises a hollow metal tube having a hole at the proximal end and two holes in the wall, said fibers entering through said hole at the proximal end and said signal output fiber exiting through one of said holes in the wall and reentering through the other.

9. A fiber-optic sensor according to claim 7, wherein said sensing portion changes transmission characteristics in response to chemical constituents of a fluid to be sensed.

10. A fiber-optic sensor according to claim 9, wherein said signal output fiber comprises a core, a cladding surrounding said core and a jacket surrounding said cladding, said sensing portion comprising said signal output fiber with said jacket removed.

11. A fiber-optic sensor according to claim 10, wherein said sensing portion further comprises a membrane, said membrane selectively allowing constituents of the fluid to be sensed to contact the signal output fiber.

12. A fiber-optic sensor according to claim 9, wherein said signal output fiber comprises a core, a cladding surrounding said core and a jacket surrounding said cladding, said sensing portion comprising said signal output fiber with said jacket and cladding removed.

13. A fiber-optic sensor according to claim 12, wherein said sensing portion further comprises a membrane, said membrane selectively allowing constituents of the fluid to be sensed to contact the signal output fiber.

14. A fiber-optic sensor system for sensing a concentration of a constituent of a fluid comprising:
   an input fiber having a proximal and distal portion;
   a reference output fiber having a proximal and distal portion;
   a signal output fiber having a proximal portion, a distal portion and a sensing portion therebetween, the distal portions of said fibers being in optical communication and said sensing portion being adjacent said distal portions and in communication with said fluid;
   a light source for transmitting light into the proximal portion of said input fiber;
   a reference sensor for sensing light from the proximal portion of said reference output fiber and providing a reference signal in response thereto;
   a signal sensor for sensing light from the proximal portion of said signal output fiber and providing a sensor signal in response thereto; and
   a dividing means for forming the ratio of the sensor signal to the reference signal, said ratio indicating the concentration of said constituent.

15. A fiber-optic sensor system according to claim 14, further comprising a concentration indicator, said concentration indicator receiving said ratio and being adapted to control an alarm.

16. A fiber-optic sensor system according to claim 14, further comprising a concentration indicator, said concentration indicator receiving said ratio and being adapted to control a chemical process.

17. A method for sensing a concentration of a constituent of a fluid comprising:
   providing an input fiber having a proximal and distal portion;
   providing a reference output fiber having a proximal and distal portion;
   providing a signal output fiber having a proximal portion, a distal portion and a sensing portion therebetween, the distal portions of said fibers being in optical communication and said sensing portion being adjacent to said distal portions and in communication with said fluid;

transmitting light into the proximal portion of said input fiber; and forming a ratio between light from the proximal portion of the signal output fiber and light from the proximal portion of the reference output fiber, said ratio indicating the concentration of said constituent.

18. A method according to claim 17, further comprising controlling an alarm in response to said ratio.

19. A method according to claim 17, further comrising controlling a chemical process in response to said ratio.

* * * * *